United States Patent
Subramaniam et al.

(10) Patent No.: US 9,809,810 B2
(45) Date of Patent: *Nov. 7, 2017

(54) GALVANOTAXIS ASSAY FOR QUANTITATIVE ASSESSMENT OF THE METASTATIC POTENTIAL OF CANCER CELLS

(71) Applicant: Ohio State Innovation Foundation, Columbus, OH (US)

(72) Inventors: Vish Subramaniam, Westerville, OH (US); Joseph West, Richwood, OH (US); Emily Alkandry, Columbus, OH (US); Mohd Nasser, Columbus, OH (US); Dinesh Ahirwar, Columbus, OH (US); Ramesh Ganju, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 82 days.

This patent is subject to a terminal disclaimer.

(21) Appl. No.: 14/765,993

(22) PCT Filed: Feb. 5, 2014

(86) PCT No.: PCT/US2014/014779
§ 371 (c)(1),
(2) Date: Aug. 5, 2015

(87) PCT Pub. No.: WO2014/123947
PCT Pub. Date: Aug. 14, 2014

(65) Prior Publication Data
US 2015/0376598 A1    Dec. 31, 2015

Related U.S. Application Data

(60) Provisional application No. 61/760,987, filed on Feb. 5, 2013.

(51) Int. Cl.
C12N 13/00    (2006.01)
A61N 2/00    (2006.01)
A61N 2/02    (2006.01)

(52) U.S. Cl.
CPC .............. *C12N 13/00* (2013.01); *A61N 2/004* (2013.01); *A61N 2/02* (2013.01)

(58) Field of Classification Search
None
See application file for complete search history.

(56) References Cited

U.S. PATENT DOCUMENTS 6,790,330 B2    9/2004    Gascoyne et al.
7,012,100 B1    3/2006    Edwards et al.
(Continued)

FOREIGN PATENT DOCUMENTS

WO    2011063458 A1    6/2011

OTHER PUBLICATIONS

Djamgoz, Mustafa B. A. et al., Directional Movement of Rat Prostate Cancer Cells in Direct-Current Electric Field: Involvement of Voltage-Gated Na+ Channel Activity, Journal of Cell Science 114 (14), 2001, pp. 2697-2705.
(Continued)

*Primary Examiner* — David W Berke-Schlessel
(74) *Attorney, Agent, or Firm* — Standley Law Group LLP

(57) ABSTRACT

An apparatus and method for accelerating and/or inhibiting the migration of cells by applying a time-varying magnetic field to induce eddy currents that promote electrotaxis (galvanotaxis) of cells without the need for chemokines or glucose. The present invention can also be used to study and quantify the metastatic potential of different cell lines.

10 Claims, 3 Drawing Sheets

(56) References Cited

U.S. PATENT DOCUMENTS

| | | |
|---|---|---|
| 7,117,034 B2 | 10/2006 | Kronberg |
| 7,700,615 B2 | 4/2010 | Edwards et al. |
| 8,019,414 B2 * | 9/2011 | Palti ............... A61K 31/337 607/3 |
| 2004/0152067 A1 | 8/2004 | Wang et al. |
| 2006/0276858 A1 | 12/2006 | Palti |
| 2009/0018613 A1 | 1/2009 | Brighton |
| 2010/0298624 A1 | 11/2010 | Becker |
| 2011/0194979 A1 | 8/2011 | Chin et al. |
| 2012/0035457 A1 | 2/2012 | Subramaniam et al. |

OTHER PUBLICATIONS

Fraser, Scott P. et al., Voltage-Gated Sodium Channel Expression and Potentiation of Human Breast Cancer Metastasis, Clinical Cancer Research 11, Aug. 1, 2005, pp. 5381-5389.

Hart, Francis X. et al., Keratinocyte Galvanotaxis in Combined DC and AC Electric Fields Supports an Electromechanical Transduction Sensing Mechanism, Bioelectromagnetics 34, Feb. 2013, pp. 85-94.

Yan, Xiaolong. et al., Lung Cancer A549 Cells Migrate Directionally in DC Electric Fields with Polarized and Activated EGFRs, Bioelectromagnetics 30, 2009, pp. 29-35.

Bullock, et al. The Effect of Induced Biphasic Pulsed Currents on Re-Epithelialization of a Novel Wound Healing Model, Bioelectromagnetics vol. 28 No. 1, Jan. 1, 2007, pp. 31-41.

Song, et al. Application of Direct Current Electric Fields to Cells and Tissues in Vitro and Modulation of Wound Electric Field in Vivo. Nature Protocols. vol. 2 No. 6., Jun. 2007, pp. 1479-1489.

Sun, et al., Electrotaxis of lung cancer cells in ordered three-dimensional scaffolds, Biomicrofluids 6, 2012.

Vianale, et al. Extremely Low Frequency Electromagnetic Filed Enhances Human Keratinocyte Cell Growth and Decreases Proinflammatory Chemokine Productions. British Journal of Dermatology. vol. 158 No. 6., Jun. 2008, pp. 1189-1196.

* cited by examiner

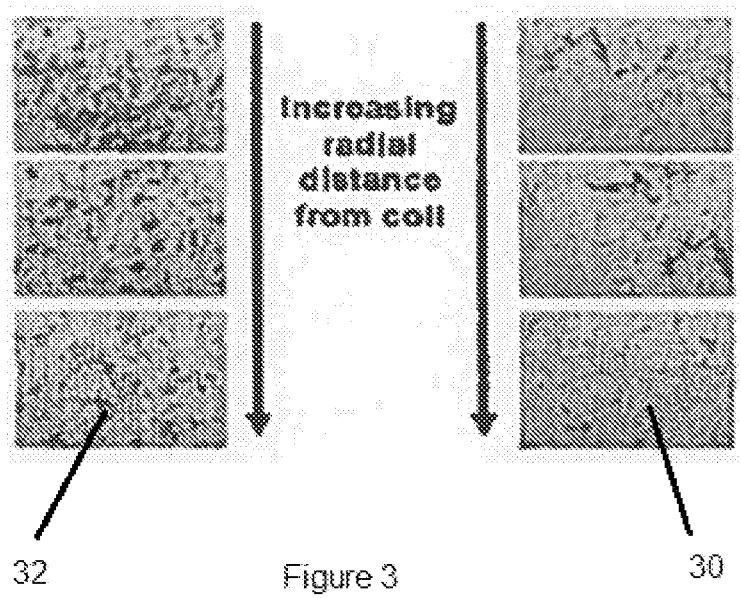
32  Figure 3  30

GALVANOTAXIS ASSAY FOR QUANTITATIVE ASSESSMENT OF THE METASTATIC POTENTIAL OF CANCER CELLS

CROSS-REFERENCE TO RELATED APPLICATIONS

This application claims priority to U.S. Provisional Application No. 61/760,987 filed on Feb. 5, 2013 and is herein incorporated by reference in its entirety.

BACKGROUND OF THE INVENTIVE FIELD

The present invention is directed to an apparatus and method of accelerating and/or inhibiting metastasis of cells by subjecting the cells to an electric field. More particularly, the present invention is directed to an apparatus and method for accelerating and/or inhibiting metastasis of cancer cells by applying a time-varying magnetic field to induce eddy currents that promote electrotaxis (galvanotaxis) of cells without the need for chemokines or glucose.

SUMMARY OF THE GENERAL INVENTIVE CONCEPT

In a preferred embodiment of the present invention, a time-varying magnetic field from an electromagnetic (EM) coil is used to induce electric fields in a modified version of Corning's Transwell permeable assay. By varying the characteristics of the excitation of the EM coil and the direction of application of the electric field, it is possible to accelerate cell migration as well as inhibit it, in the presence or absence of chemokines. The modified assay provides a novel method to study and quantify metastasis. For example, metastatic cell lines can be compared to each other in these assays by subjecting them to the EM fields and counting the number of cells that migrate across the permeable membrane. Comparisons between cell lines can also be drawn and quantified in the presence of both EM fields and chemokines. Quantification can be accomplished by counting the cells or by digitizing the image and calculating cell coverage areas on the bottom of the membrane. In one embodiment, the EM coil is driven using a function generator using a 20 Vpp, 100 kHz, sawtooth wave with a sharp ~50 ns drop to generate a rapidly time-varying magnetic field.

In an exemplary embodiment of the present invention, the method is comprised of the steps of:
providing an electromagnetic coil having a first end and a second end;
connecting the electromagnetic coil to a function generator;
applying a time-varying sawtooth voltage waveform to the electromagnetic coil;
inducing a time-varying electric field around the electromagnetic coil;
placing the electromagnetic coil adjacent to the location of cancer cells with the direction of the induced electric field directed towards the cancer cells;
orientating the placement of the electromagnetic coil so that the direction of the electric field is directed away from an area of healthy cells; and
inhibiting migration of the cancer cells using the induced electric field.

In one embodiment the waveform applied to the coil is a 20 volts peak to peak, 100 kHz sawtooth waveform with a 50 ns drop off at its trailing edge that induces a rapidly time-varying magnetic field.

It is appreciated that the characteristics of the waveform can be adjusted to control metastasis.

Furthermore, the following additional steps may be taken according to one embodiment of the invention for studying and quantifying the metastatic potential of cell lines:
placing the electromagnetic coil in between a first row of a plurality of assay wells and second row of a plurality of assay wells;
providing a plurality of well inserts having a porous membrane;
placing one of the well inserts into each of the plurality of assay wells so that the wells are divided into a lower and upper compartment;
placing a medium into each of the plurality of assay wells;
placing a predetermined line of cancer cells into each of the assay wells;
allowing the predetermined lines of cancer cells to settle on top of the porous membranes;
taking an image of the porous membrane after the step of inducing a time-varying electric field;
quantifying metastatic potential of the predetermined lines of cancer cells; and
introducing a predetermined chemokine into each of the assay wells.

The foregoing and other features and advantages of the present invention will be apparent from the following more detailed description of the particular embodiments, as illustrated in the accompanying drawings.

BRIEF DESCRIPTION OF THE DRAWINGS

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

In addition to the features mentioned above, other aspects of the present invention will be readily apparent from the following descriptions of the drawings and exemplary embodiments, wherein like reference numerals across the several views refer to identical or equivalent features, and wherein:

FIG. 3 illustrates microscopic images of the bottom of a permeable membrane showing migration of metastatic cancer cells across the membrane.

DETAILED DESCRIPTION OF EXEMPLARY EMBODIMENT(S)

Figure 1:
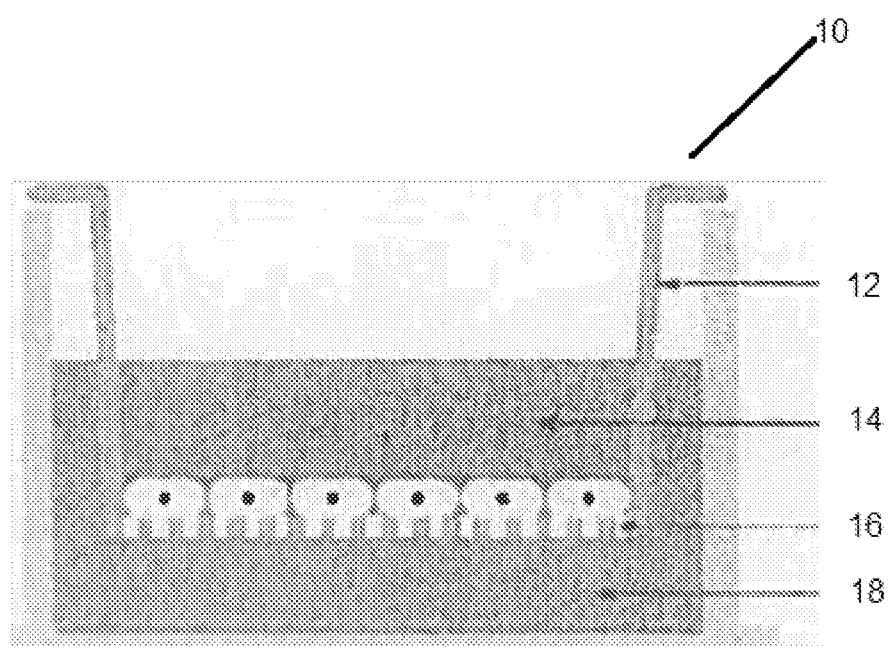
FIG. 1 illustrates an assay with an insert with a porous membrane.

An assay that is commonly used to evaluate the response of cancer cells to chemokines and chemotherapy drugs is Corning's Transwell Permeable Support assay 10. In this assay, inserts 12 with porous membranes 16 at the bottom are placed into standard plate wells as shown in FIG. 1. With a suitable chemokine placed in the lower compartment 18, a monolayer of cells can be made to migrate from the upper compartment 14 to the lower compartment. In other words, by placing suitable chemokines in the lower compartment, the infiltration capabilities of cancer cells may be studied by observing the number that migrate from the membrane side in contact with the upper compartment to the membrane side in contact with the lower compartment. This is an example of chemotaxis, which refers to the motility of cells under the action of a gradient in the concentration of a chemical substance such as growth factors or chemokines. Biological cells move in response to other forces as well, such as electrical forces. The directional movement of biological cells in the presence of an applied electric field is known as Galvanotaxis or electrotaxis. This effect is named after Luigi Galvani, who in the 18$^{th}$ century discovered bioelectricity. The majority of experiments related to galvanotaxis over the past two centuries have involved steady electric fields applied via electrodes placed in contact with the medium containing cells (usually, the electrodes are in contact with the medium containing the cells through agar filled tubes and the applied electric field is usually DC).

The system and method of the present invention is used for inducing electric fields in the medium containing cells, for example the Corning's Transwell permeable assay, by applying time-varying magnetic fields. The method uses electromagnetic (EM) induction to induce electric fields and eddy currents in the medium to promote galvanotaxis of cells without the need for chemokines or glucose. This is of significance since cancer cells are known to respond to externally applied electric fields so that they can be distinguished from normal cells. Moreover, metastatic potential of different cancer cells may be quantitatively evaluated by counting the number of cells migrated across the membrane, so that this can form the basis for a new assay.

Figure 2:
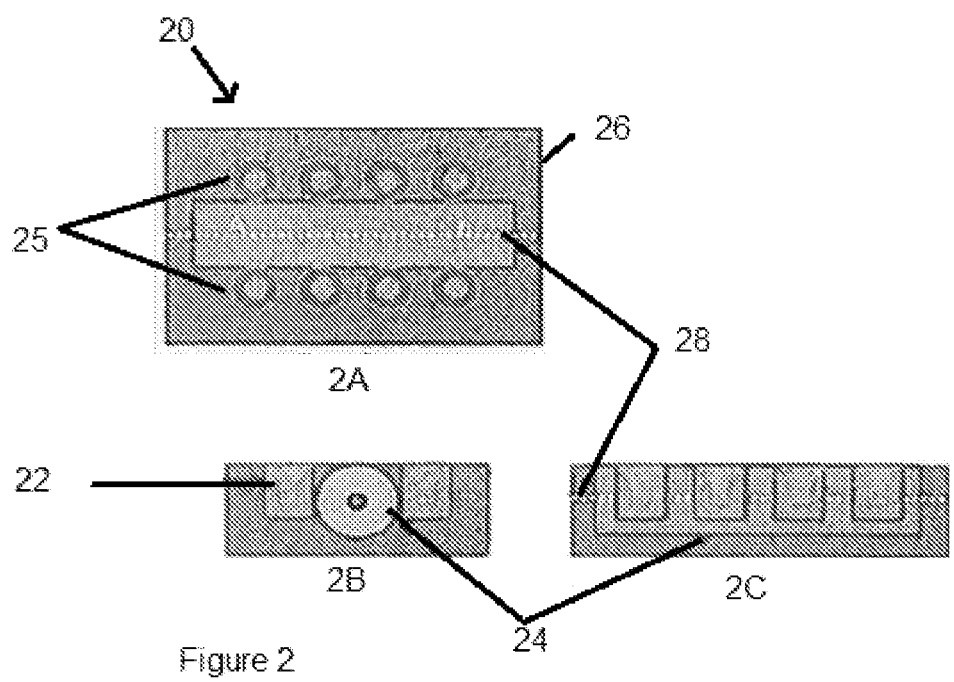
FIGS. 2A-2C illustrate one embodiment of the apparatus of the present invention having an EM coil placed between two rows of wells.

In one embodiment, a SCP2 cell line cultured in Dulbecco's Modified Eagle Medium (DMEM) without serum with a density of $3.3 \times 10^6$ cells/mL is used. This cell line is a highly metastatic estrogen receptor (negative) breast cancer cell line derived from the MDA-MB-231 cell line. In this embodiment, 150 µL of the medium containing this cell line (~$4.95 \times 10^4$ cells) is pipetted into the upper compartment of a single Transwell permeable insert (equipped with a 6 µm filter) while the lower compartment has 200 µL of the same medium but with no cells. The single plate well with the insert is then placed adjacent to a horizontally oriented electromagnetic (EM) coil (R~22Ω, L=10 mH) and fixture as shown in FIG. 2.

FIGS. 2A-2C illustrate schematics of one embodiment of the apparatus 20 of the present invention with modified Corning Transwell plates 22 with the electromagnetic (EM) coil 24 placed in the middle of two rows 25 of wells. These components are placed in a holder 26 as shown. The center line 28 of the coil is illustrated by the dashed line as shown. The glass wells are preferably configured with offset holes to accommodate Corning Transwell permeable inserts with dimensions such that the centerline of the coil is at the same elevation as the membrane of the insert. FIG. 2A illustrates a top view of the apparatus. FIG. 2B illustrates a front view and FIG. 2C illustrates a side view. In another embodiment, a single well with one insert is used, adjacent to the coil. Once the cells are allowed to settle onto the upper surface of the permeable membrane (see FIG. 1), the entire apparatus is placed inside an incubator (at 37° C. with 5% $CO_2$) for a period of 12 hours. As control case, a similar plate well with similar permeable insert and with the same highly metastatic cells, but not exposed to the EM coil, is also placed in the incubator. Both setups are imaged after a period of 12 hours.

In one embodiment, the EM coil is driven using a function generator using a 20 Vpp, 100 kHz, sawtooth wave with a sharp ~50 ns drop to generate a rapidly time-varying magnetic field with components $B_r$ and $B_z$. By Faraday's law these temporally varying magnetic fields from the EM coil induce an electric field $E_\theta$ in the medium containing the cells due to the small but non-zero electrical conductivity of the medium. Because of the placement of the plate well relative to the coil, this results in a vertically directed electric field across the membrane, but with $E_\theta$ decaying radially with increasing distance from the coil. At the driving frequency of 100 kHz, $E_\theta$ switches directions back and forth (up and down) across the membrane, but with a non-equal component directed downward or upward depending on the side of the coil.

FIG. 3 illustrates microscopic images of a bottom of the permeable membrane showing differences between a control case 30 and a case where an EM field is applied 32. FIG. 3 shows coarse scale microscope images of a bottom of the permeable membrane in the control as well as in the insert subjected to the EM field. As illustrated by the figure, application of the time-varying magnetic field results in induced electric fields which increase migration of the metastatic cancer cells across the membrane even in the absence of chemokines. In contrast, the control case (with no applied electric field) results in the typically observed random migration patterns. By selecting a different set of characteristics for the driving waveform (e.g. waveform type, peak to peak voltage, and frequency) migration of cells can be reduced as shown in FIG. 2 by simply reversing the field. It should be noted that this result is of significance for cancer treatment where inhibition of metastasis in tumors may have beneficial effects in vivo.

In addition to implications for hindering metastasis, Corning's Transwell assay can be modified to provide a method to quantify metastasis. For instance, metastatic cell lines can be compared to each other in these assays by subjecting them to the same EM fields and counting the number of cells that migrate across the permeable membrane. The quantification can be accomplished by counting the cells or by digitizing the image and calculating cell coverage areas on the bottom of the membrane. The effects of various drugs and chemokines may also be evaluated in the presence of EM fields so as to decipher the effects of in vivo endogenous electric fields that may adversely affect the therapeutic effects of chemotherapy drugs.

In summary, a time-varying magnetic field from an electromagnetic (EM) coil is used to induce electric fields in a modified version of Corning's Transwell permeable assay. Preliminary in vitro experiments on the highly metastatic SCP2 breast cancer cell lines show that cell migration across the membrane can be significantly increased compared to the control case where no EM field is applied. By varying the characteristics of the excitation of the EM coil, it is possible to accelerate metastasis as well as inhibit it. This degree of control without the use of chemokines suggests a natural means of quantifying the metastatic potential of different cancer cells as well as a natural means of comparing them with the motility of normal cells.

While certain embodiments of the present invention are described in detail above, the scope of the invention is not to be considered limited by such disclosure, and modifications are possible without departing from the spirit of the invention as evidenced by the following claims:

What is claimed is:

1. A method for controlling cell migration comprising the steps of:

providing an electromagnetic coil having a first end and a second end;

connecting the electromagnetic coil to a function generator;

applying a time-varying voltage waveform to the electromagnetic coil;
inducing a time-varying electric field around the electromagnetic coil;
placing the electromagnetic coil adjacent to, and without contacting, the location of cancer cells;
directing the induced electric field along an axis of migration of the cancer cells;
orientating the placement of the electromagnetic coil to control the direction of the induced electric field; and
reducing the migration of the cancer cells using the induced electric field.

2. A method according to claim 1 further comprising the step of:
inducing eddy currents near the location of the cancer cells.

3. A method according to claim 1, wherein the time-varying waveform is a sawtooth waveform.

4. A method according to claim 1, wherein the time-varying waveform is a 20 volts peak to peak, 100 kHz sawtooth waveform with a 50 ns drop off at its trailing edge.

5. A method according to claim 4, wherein the sawtooth waveform has a sharp drop and wherein the induced electric field is a rapidly time-varying magnetic field.

6. A method for controlling cell migration comprising the steps of:
providing an electromagnetic coil having a first end and a second end;
connecting the electromagnetic coil to a function generator;
applying a time-varying sawtooth voltage waveform to the electromagnetic coil;
inducing a time-varying electric field around the electromagnetic coil;
placing the electromagnetic coil adjacent to, and without contacting, the location of cancer cells;
directing the induced electric field along an axis of migration of the cancer cells, and wherein the induced electric field switches direction along the axis of migration with a non-equal component directed towards or away from a direction of migration;
orientating the placement of the electromagnetic coil to control the direction of the nonequal component of the induced electric field; and
reducing migration of the cancer cells using the induced electric field.

7. A method according to claim 6, wherein the time-varying waveform is a 20 volts peak to peak, 100 kHz sawtooth waveform with a 50 ns drop off at its trailing edge.

8. A method according to claim 6, wherein the sawtooth waveform has a sharp drop and wherein the induced electric field is a rapidly time-varying magnetic field.

9. A method according to claim 6, further comprising the steps of:
placing the electromagnetic coil in between a first row of a plurality of assay wells and second row of a plurality of assay wells;
providing a plurality of well inserts having a porous membrane;
placing one of the well inserts into each of the plurality of assay wells so that the wells are divided into a lower and upper compartment;
placing a medium into each of the plurality of assay wells;
placing a predetermined line of cancer cells into each of the assay wells; and
allowing the predetermined lines of cancer cells to settle on top of the porous membranes.

10. A method according to claim 1, wherein the induced electric field switches direction along the axis of migration with a non-equal component directed towards or away from a direction of migration; and further comprising the step of:
orientating the placement of the electromagnetic coil to control the direction of the nonequal component of the induced electric field.

\* \* \* \* \*